US012805701B2

(12) United States Patent
Shahmoon et al.

(10) Patent No.: US 12,805,701 B2
(45) Date of Patent: Nov. 24, 2026

(54) DISPOSABLE ENDOSCOPE

(71) Applicant: ZSQUARE LTD., Petah Tikva (IL)

(72) Inventors: Asaf Shahmoon, Petah Tikva (IL); Zeev Zalevsky, Rosh HaAyin (IL); Amihai Meiri, Ramat Hasharon (IL); Vacheslav Starobinsky, Netanya (IL)

(73) Assignee: ZSQUARE LTD., Petah Tikva (IL)

( * ) Notice: Subject to any disclaimer, the term of this patent is extended or adjusted under 35 U.S.C. 154(b) by 440 days.

(21) Appl. No.: 17/917,606

(22) PCT Filed: Mar. 23, 2021

(86) PCT No.: PCT/IL2021/050323

§ 371 (c)(1),
(2) Date: Oct. 7, 2022

(87) PCT Pub. No.: WO2021/214746

PCT Pub. Date: Oct. 28, 2021

(65) Prior Publication Data

US 2023/0148839 A1 May 18, 2023

Related U.S. Application Data

(60) Provisional application No. 63/012,164, filed on Apr. 19, 2020.

(51) Int. Cl.
*A61B 1/00* (2006.01)
*A61B 1/005* (2006.01)

(52) U.S. Cl.
CPC ...... *A61B 1/00103* (2013.01); *A61B 1/00135* (2013.01); *A61B 1/00167* (2013.01); *A61B 1/0052* (2013.01)

(58) Field of Classification Search
CPC ............ A61B 1/00103; A61B 1/00135; A61B 1/00105; A61B 1/00066; A61B 1/0052; A61B 1/0051
See application file for complete search history.

(56) References Cited

U.S. PATENT DOCUMENTS 4,919,112 A * 4/1990 Siegmund ............ A61B 1/0052 600/146
5,402,768 A * 4/1995 Adair ................. A61B 1/00158 600/110

(Continued)

FOREIGN PATENT DOCUMENTS

DE 10 2015 015041 5/2017
JP H7-51217 2/1995

(Continued)

OTHER PUBLICATIONS

International Search Report for PCT Application No. PCT/IL2021/050323 dated Jun. 27, 2021.

(Continued)

*Primary Examiner* — Timothy J Neal
(74) *Attorney, Agent, or Firm* — PEARL COHEN LLP

(57) ABSTRACT

An endoscope device comprises a reusable unit and a disposable unit. The reusable unit comprises a receiver adapted to receive image data and the disposable unit comprises an insertion tube. The insertion tube comprises an optical guide to image a distal object and a housing that is adapted to accommodate the reusable unit. The reusable unit is adapted to be disposed inside the housing and to be mechanically secured in it. The receiver is adapted to receive an optical image from the optical guide and to convert it to digital image data.

11 Claims, 10 Drawing Sheets

(56) References Cited

U.S. PATENT DOCUMENTS

| | | | | |
|---|---|---|---|---|
| 5,704,892 | A | 1/1998 | Adair | |
| 6,692,432 | B1 * | 2/2004 | Yarush | A61B 1/00108 600/179 |
| 2008/0208006 | A1 | 8/2008 | Farr | |
| 2008/0249355 | A1 * | 10/2008 | Birnkrant | A61B 1/267 600/169 |
| 2010/0261967 | A1 * | 10/2010 | Pacey | A61M 16/0495 600/188 |
| 2011/0130632 | A1 | 6/2011 | Mcgrail et al. | |
| 2013/0345503 | A1 * | 12/2013 | Friedrich | A61B 1/00034 600/103 |
| 2014/0275763 | A1 * | 9/2014 | King | A61B 1/00105 600/110 |
| 2015/0011825 | A1 * | 1/2015 | L'Helgoual'ch | A61B 1/0669 600/109 |
| 2019/0104928 | A1 | 4/2019 | Murray | |
| 2019/0246873 | A1 | 8/2019 | Lu et al. | |
| 2019/0374095 | A1 | 12/2019 | Lord et al. | |

FOREIGN PATENT DOCUMENTS

| | | |
|---|---|---|
| JP | 2007-236812 | 9/2007 |
| JP | 2011-104004 | 6/2011 |
| JP | 2012-55342 | 3/2012 |
| WO | WO 2009/078070 | 6/2009 |
| WO | WO 2015/050101 | 4/2015 |
| WO | WO 2019/118484 | 6/2019 |

OTHER PUBLICATIONS

Office Action for JP Application No. 2022-557067 dated Jan. 21, 2025.

* cited by examiner

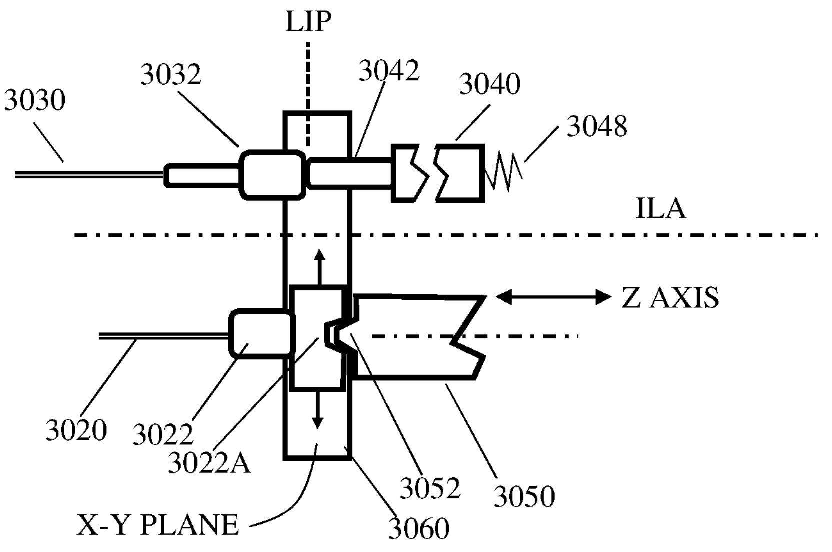
Fig. 3A1
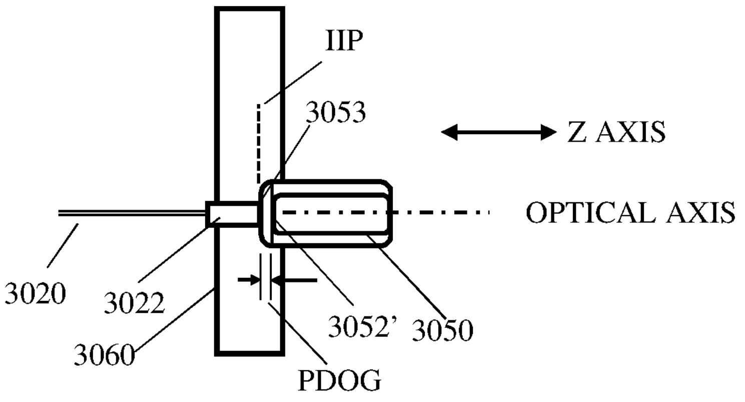
Fig. 3A2

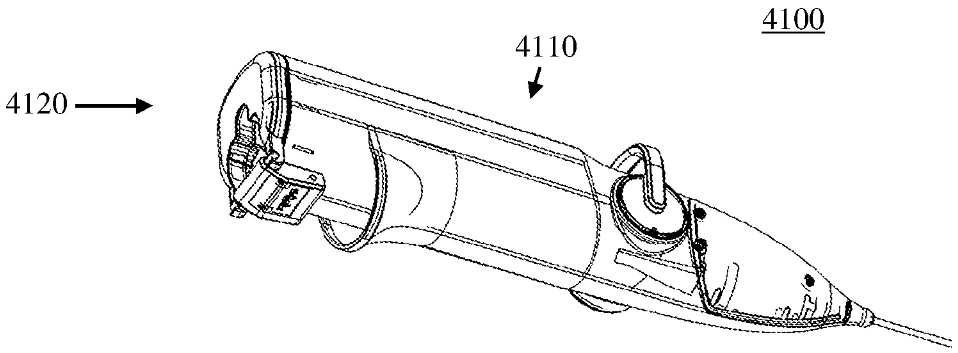
Fig. 4C
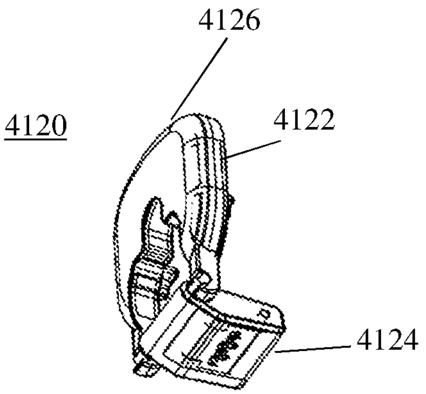
Fig. 4C2
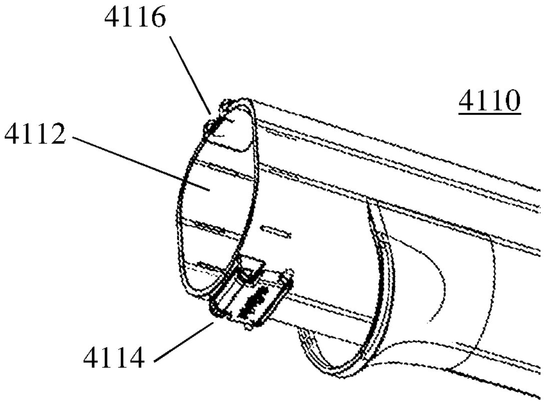
Fig. 4C1

DISPOSABLE ENDOSCOPE

CROSS-REFERENCE TO RELATED APPLICATIONS

This application is a US National Phase Application of PCT International Patent Application No. PCT/IL2021/050323, International Filing Date Mar. 23, 2021, claiming the benefit of US Provisional Application No. 63/012,164, filed Apr. 19, 2020, which is hereby incorporated by reference.

BACKGROUND OF THE INVENTION

Endoscopes may be reusable, yet, for the sake of hygienic requirements, the device must be washed or otherwise sterilized after use with each patient. There is a need for a device and method enabling reuse of an endoscope without tampering with the hygienic requirements and with minimized repeating sterilization operations.

SUMMARY OF THE INVENTION

An endoscope device is disclosed comprising a disposable unit that includes an endoscopic insertion tube comprising an optical guide, having a proximal end and a distal end, for imaging a distal object. The disposable unit may also include an interface unit and a housing defining a confined space. The endoscope device may also include a reusable unit configured to be disposed and secured inside the housing of the disposable unit and comprising a receiver to receive, via the interface unit, image data of the imaged distal object.

In some embodiments of the invention, the interface unit includes an optical coupler.

In some embodiments of the invention, the receiver is adapted to receive an optical image from the optical guide via the optical coupler and to convert it to digital image data.

In some embodiments of the invention, the receiver includes an optical sensor.

In some embodiments of the invention, the disposable unit further includes a navigation mechanism for manipulating the distal tip of the insertion tube.

In some embodiments of the invention, the reusable unit further includes a navigation lever to operate the navigation mechanism.

In some embodiments of the invention, the endoscope device further includes a light source.

In some embodiments of the invention, the light source is disposed within the reusable unit, wherein the insertion tube further comprises an illumination guide to guide light from the illumination source to the distal end of the insertion tube.

In some embodiments of the invention, the light source is disposed at the distal end of the insertion tube.

In some embodiments of the invention, the optical guide includes a multicore fiber.

In some embodiments of the invention, the endoscope device further includes a focusing unit for enabling focusing the image by means of controlling the distance between the proximal end of the optical guide and the receiver.

In some embodiments of the invention, the endoscope device includes an aligning device for aligning of the proximal end of the optical guide with an optical axis of the receiver.

In some embodiments of the invention, the endoscope device further includes an extendable sterilization protecting flexible sleeve configured to be rolled off an aft end of the disposable unit and enclose a cable leading from the reusable unit to a control unit.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 3A1 and 3A2 are simplified schematic illustrations demonstrating aspects of the interface between a disposable unit and a reusable unit, according to some embodiments of the invention;

FIGS. 4C, 4C1 and 4C2 are schematic partial isometric illustrations of a back cover of a disposable endoscope unit, according to embodiments of the invention;

Figure 1A:
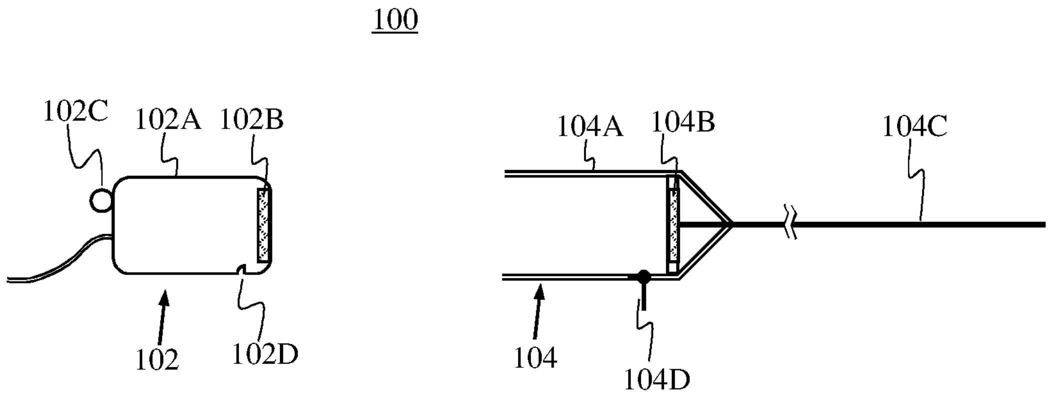
FIGS. 1A and 1B are schematic illustrations of an endoscope comprising a reusable unit and a disposable unit, in disassembled (1A) and in assembled (1B) positions, respectively, according to some embodiments of the present invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

According to some embodiments of the invention an endoscope may be reusable in an affordable manner, meaning with minimized sterilization efforts and without tampering with hygienic requirements. According to some embodiments of the invention, only a part of the endoscope, e.g., the endoscope insertion tube, may be disposable. The disposable insertion tube of the endoscope may comprise only minimal essential elements, thereby minimizing the production costs for the disposable insertion tube. Use of a disposable insertion tube may be highly advantageous as it may decrease the risk for cross contamination between patients as well as reduce the need for a sterilization process, while requiring replacement of only a portion of an endoscope (the disposable insertion tube).

Some embodiments of the present invention relate to endoscopes, multicore endoscope fibers and configuration and operation methods. Multicore fibers, according to some embodiments, may have a large number (e.g., hundreds or thousands) of cores and may incorporate working channel(s) and/or additional fibers. The fiber used may be provided in different optical configurations to capture images of tissue and objects at the distal tip of the endoscope, and to enhance a wide range of optical characteristics of the obtained images, such as resolution, field of view, depth of field, wavelength ranges, etc. Near-field imaging as well as far-field imaging may be implemented in the endoscopes, according to some embodiments of the invention, and the respective optical features may be utilized to optimize imaging. Optical elements may be used at the distal tip, or the distal tip may lack any lenses. Diagnostics and optical treatment feedback loops may be implemented, and illumination may be adapted to yield full color images, depth estimation, enhanced field of view and/or depth of field and additional diagnostic data.

Various embodiments of multicore endoscope fibers may be used. An endoscope, according to some embodiments of the present invention, may implement far field imaging, i.e., have the image formed at the proximal end of the endoscope fiber, while another endoscope, according to some embodiments, may implement near field imaging, i.e., have the image formed at the distal end of the endoscope. Both far field and near field implementations, may have distal optical elements between the imaged objects or tissues and the distal tip of the endoscope, or may operate without such distal optical elements. Each of the four combinations (far field with and without distal optical elements and near field with and without distal optical elements) has different features, advantages and disadvantages, and may be selected according to specific implementation scenarios. Alternation of the combination may be carried out between applications or in real time, to combine advantages of different configuration types. It is further noted that endoscopes may be designed to have several combinations, e.g., a part of the fiber face (or certain fiber modules) having distal optics for imaging far objects and another part of the fiber face (or other fiber modules) lacking distal optics for microscopic imaging.

Endoscopes, according to some embodiments, may lack any optical elements at the distal tip. Such lens-less embodiments may implement either far-field or near-field imaging, and may utilize structural features to enhance optical resolution, apply super-resolution methods and retrieve wave front information while reducing crosstalk between the cores.

Endoscopes, according to some embodiments of the invention, may have full tip cross sections or have working channel(s) within the imaging fiber characterized by different configurations and uses, integrating additional fibers etc., in which case the cores and optical elements may be configured to overcome reduction of the field of view due to the incorporation of the working channel.

Various configurations of large number of cores in the endoscope fiber, according to some embodiments of the invention, may provide solutions to various issues such as reducing crosstalk between the fibers, overcoming material losses, achieving enhanced resolution by different methods, providing required mechanical characteristics and optimizing the imaging performances of the endoscope fibers. Endoscopes, according to some embodiments of the invention, may serve for different purposes, e.g., may be designed as a laparoscope or an ureteroscope, etc.

A micro endoscope, according to some embodiments of the invention, may be constructed from a large number of cores (e.g., one hundred cores or more, hundreds of cores, thousands of cores, in certain embodiments tens or hundreds of thousand cores per fiber or fiber module, reaching over a million cores in certain fiber endoscopes), where each core may be responsible for transferring a single or a large number of spatial degrees of freedom out of which at the output, proximal end (the end which is external to the patient body), a high resolution color image may be constructed. Multi-core fiber, according to some embodiments of the present invention, may exhibit a high degree of flexibility in its optical design, which may be utilized and adapted for specific applications, for example for ureteroscopes with a large working channel and a small external diameter or for laparoscopes with a very high resolution obtained at a small external diameter.

According to some embodiments of the invention, the endoscope may be divided into two main parts: a reusable endoscope handle that may include the majority of and the more expensive functionalities of the endoscope, such as the more complicated and expensive optical units (e.g. camera, image initial processing means and electronics), and a detachable and disposable endoscope insertion tube (or head) that may include a simpler and relatively cheap optical setup, endoscope image conducting guide, such as an optical fiber or a fiber bundle (e.g., multicore fiber, with a multitude of cores) and optionally lighting guide or guides (e.g., one or a plurality of cores in the fiber) for guiding illumination to the distal end of the insertion tube.

The endoscope insertion tube may include a fiber-based light conduit means and specific optic and mechanics connecting means, adapted to firmly attach the disposable endoscope insertion tube to the reusable endoscope handle. In some embodiments, the light source may be disposed at the distal end of the endoscope, e.g., using a suitable LED (light emitting diode) as a light source. A universal mounting interface at the front end of the endoscope handle may allow the use of application specific, exchangeable endoscope insertion tubes having different capabilities. An electronic-dense reusable handle allows functionality with various different single-use disposable insertion tubes. The disposable endoscope insertion tube may comprise a housing located at a proximal end of the insertion tube, adapted to accommodate and envelope the endoscope handle in a way that protects it, shielding it from outside physical contact and contamination, and preserving its sterilization. The entire endoscope may be covered with a sealable (e.g., plastic, rubber) cover covering both parts (disposable and reusable) including the electrical cable connected to the reusable handle. When desired, e.g., at the end of usage, the handle may be detached from the disposable endoscope insertion tube and extracted from the housing, while the disposable endoscope insertion tube with the housing is disposed of or discarded.

The connection between the handle and the disposable endoscope insertion tube may include a mechanical connector that could be based on various configurations including magnets located at both sides of the connecting interface, mechanical rotation-based clips, mechanical translation-based clips (catching both parts when rotating one part in respect to the other), screw like/bayonet-type connection based on rotation, and the like.

Figure 1B:
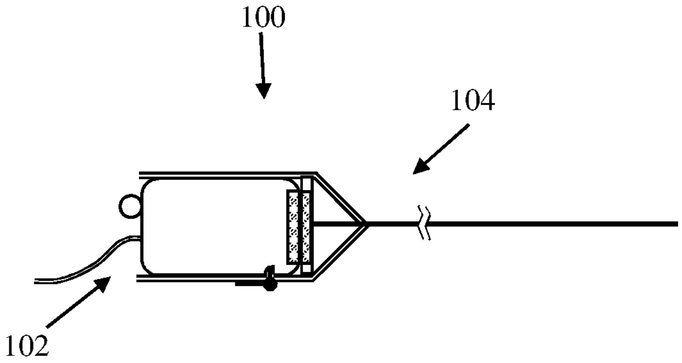

Reference is made now to FIGS. 1A and 1B, which are schematic illustrations of endoscope 100 in disassembled and in assembled positions, respectively, according to some embodiments of the present invention. Endoscope 100 comprises two main parts: a reusable endoscope handle 102 and a disposable endoscope insertion tube 104. Disposable endoscope insertion tube 104 comprises endoscope handle housing 104A, adapted to sealingly accommodate reusable endoscope handle 102 in it. Disposable endoscope insertion tube 104 further comprises endoscope handle interface unit 104B, endoscope optical probe unit 104C and endoscope locking means 104D.

Reusable endoscope handle 102 comprises endoscope body 102A which may comprise electronics, power source, communication unit, etc., according to a specific design. Reusable endoscope handle 102 further comprises endoscope disposable insertion tube interface unit, adapted to support and enable transfer, communication and exchange of optical and electrical signals and data, according to a given specific design. Interface unit 102B may provide, according to some embodiments, non-contact interface, e.g., using only optical coupling with disposable endoscope insertion tube. In such embodiments, disposable insertion tube may require inclusion of power source (not shown in FIGS. 1A and 1B).

Reusable endoscope handle 102 further comprises pull-out means 102C adapted to enable pulling reusable handle 102 out of housing 104A in a sterilization-preserving manner. After handle 102 is pulled out of housing 104A, disposable insertion tube 104 may be disposed of and reusable handle 102 may be re-used in a future procedure.

When handle 102 is inserted into housing 104A, in preparation for medical procedure, handle 102 should, in a preferred embodiment, be inserted fully into the housing so that locking means 104D can be operated to lock handle 102 securely inside housing 104A, e.g., by pushing a jig into recess 102D made in the outer face of handle 102/using a back cover that will lock the system.

When handle 102 is properly located and locked inside housing 104A, interface units 102B and 104B should, in a preferred embodiment, be placed against each other in a way that enables connection, communication and signals exchange between handle 102 and disposable insertion tube 104, according to the specific design. In some embodiments, the interface may be made with no mechanical/electrical connection, relying on, for example, optical coupling.

Figure 2A:
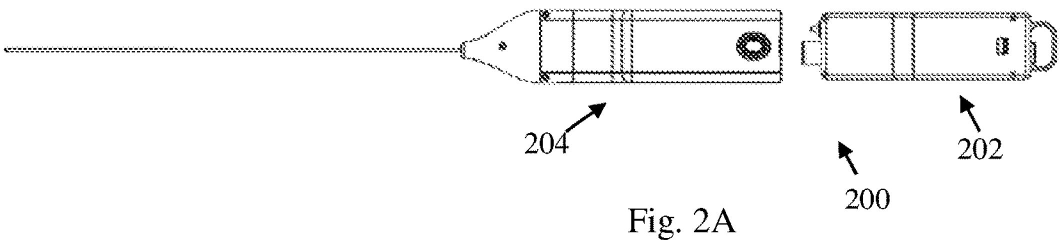
FIGS. 2A-2D are schematic illustrations of an endoscope with reusable and disposable units shown in top view and side view in disassembled position, and in top and side view in assembled position, respectively, according to some embodiments of the invention.
Figure 2B:
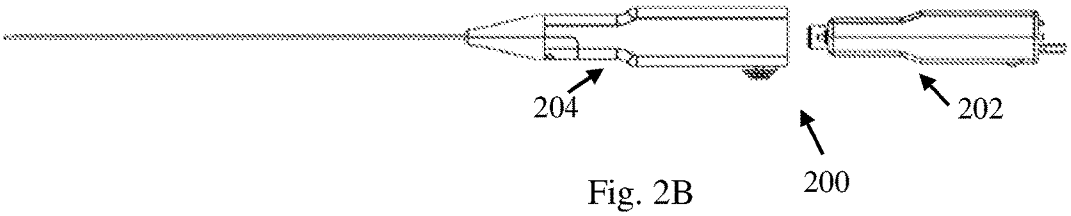
Figure 2C:
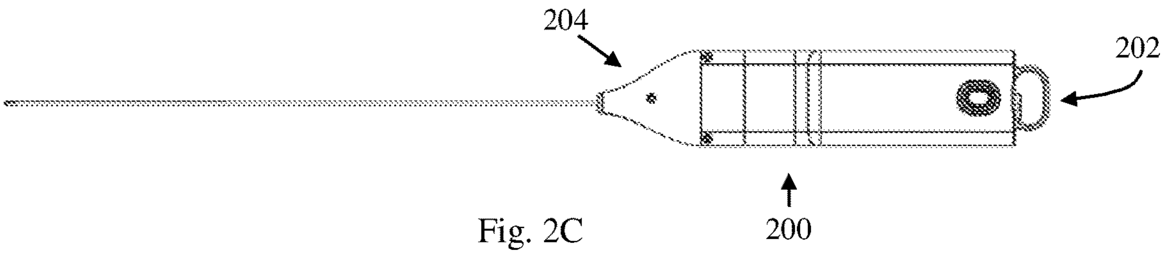
Figure 2D:
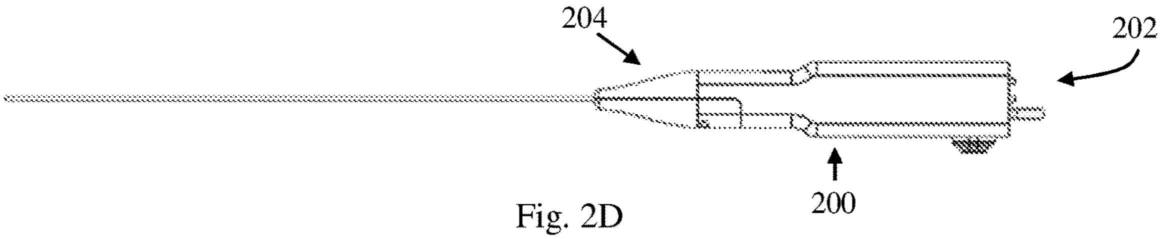

Reference is made now to FIGS. 2A, 2B, 2C and 2D, which are schematic illustrations of endoscope 200 with reusable and disposable units shown in front view and side view in disassembled position, and in front and side view in assembled position, respectively, according to some embodiments of the invention Similar to endoscope 100, endoscope 200 comprises two main parts: a reusable unit 202 and a disposable unit 204. As seen in FIGS. 2A and 2B, the shape and size of reusable unit 202 fits slidably into a housing made in the major part of the rear end of disposable unit 204. When reusable unit 202 is inserted into the housing in disposable unit 204, reusable unit 202 is enclosed fully in disposable unit 204.

Figure 2E:
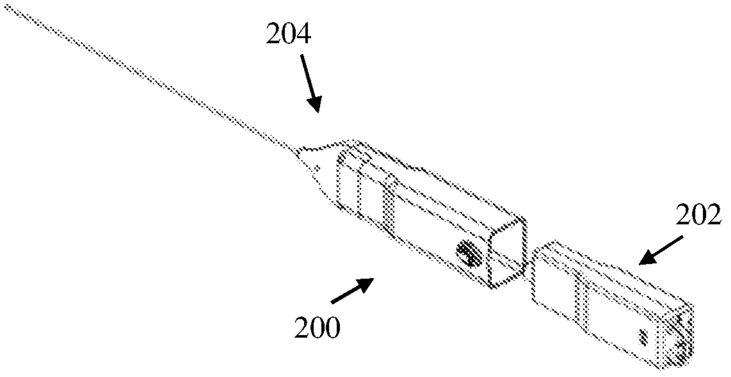
FIGS. 2E and 2F are isometric 3D views of endoscope 200 shown in disassembled position and in assembled position, respectively, according to some embodiments of the invention.
Figure 2F:
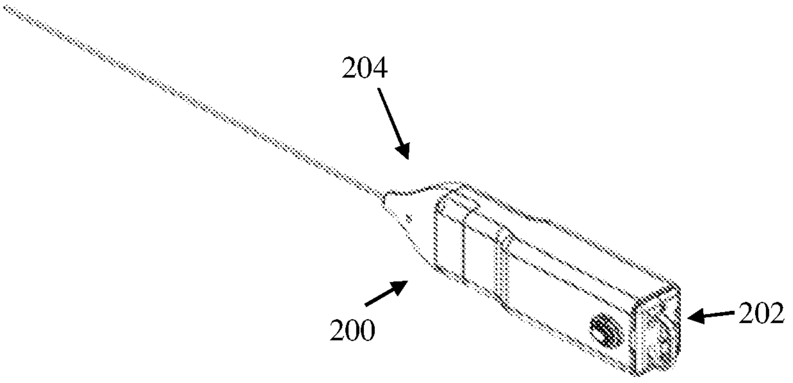

Reference is made now also to FIGS. 2E and 2F, which are isometric 3D views of endoscope 200 shown in disassembled and in assembled position, respectively, according to some embodiments of the invention. The selected viewing angle of FIGS. 2E and 2F clearly demonstrates the complete accommodation of reusable unit 202 inside the housing made in disposable unit 204.

Figure 3:
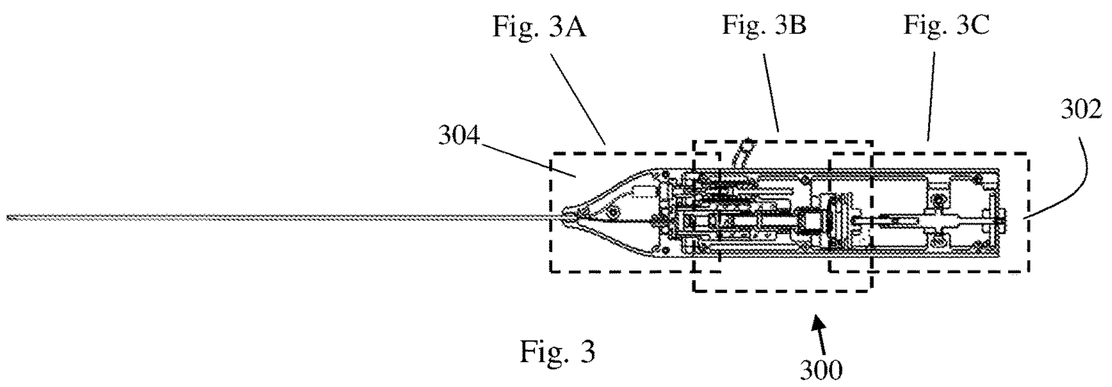
FIG. 3 is a schematic illustration of the inside elements of a reusable part and of a disposable part of an endoscope in general view, according to some embodiments of the invention.

Reference is made now to FIG. 3, which is a schematic illustration of the inside elements of the reusable part 302 and disposable part 304 of endoscope 300 in general view, according to some embodiments of the invention. In order to enable clear understanding of the embodiment presented in FIG. 3, the inside view of endoscope 300 is partitioned into three different views: the frontmost view (the view that is closest to the connection to the endoscope insertion tube) as depicted in detail in FIG. 3A, the central view as depicted in FIG. 3B, and the rearmost view as depicted in FIG. 3C.

Figure 3A:
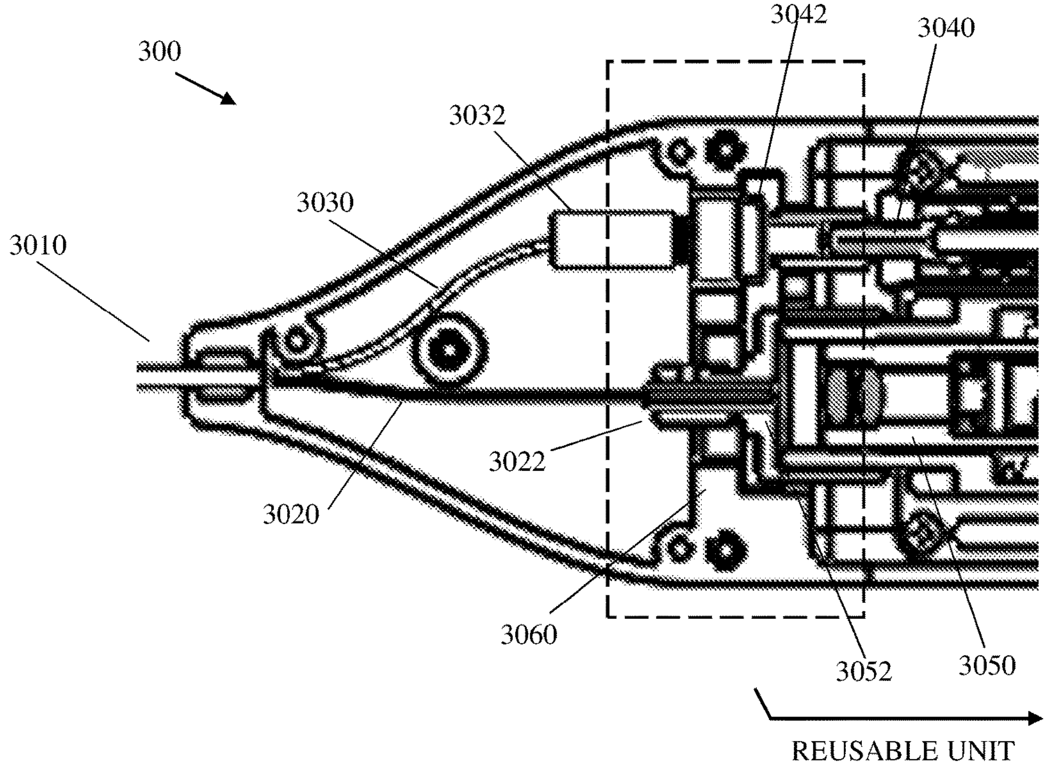
FIG. 3A is a schematic illustration of the inside elements of the front end of an endoscope, according to some embodiments of the invention.
Figure 3B:
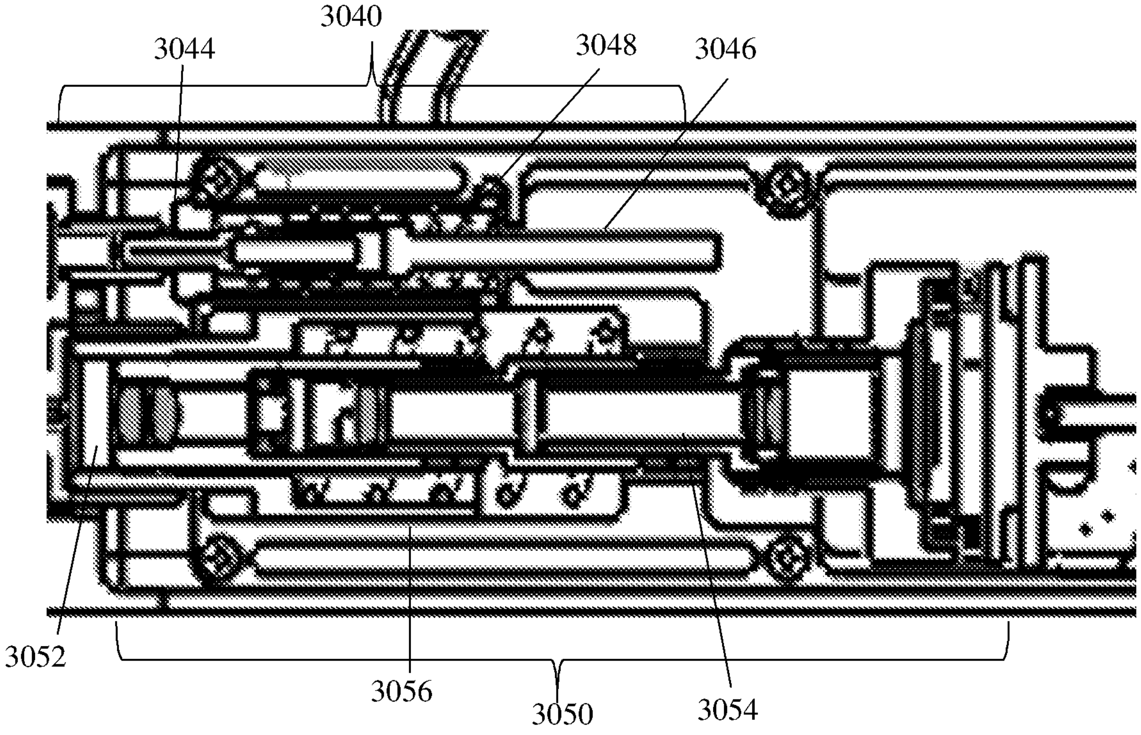
FIG. 3B is a schematic illustration of the inside elements of the central part of an endoscope, according to some embodiments of the invention.
Figure 3C:
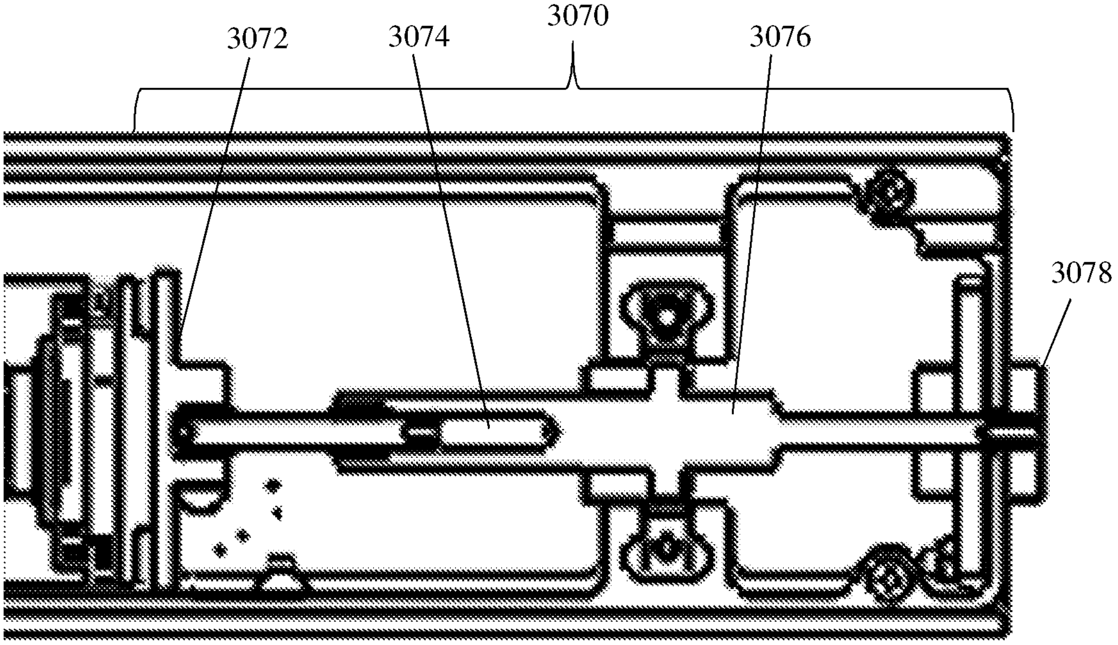
FIG. 3C is a schematic illustration of the inside elements of the rear part of an endoscope, according to some embodiments of the invention.

Reference is made now to FIG. 3A, which is a schematic illustration of the inside elements of the front end of endoscope 300, according to some embodiments of the invention. Endoscope insertion tube 3010 exits the frontmost end of endoscope 300, and in the inside, insertion tube 3010 splits to fiber/multicore fiber 3020 and light waveguide 3030. Light waveguide 3030 ends with light waveguide interface unit 3032, e.g., optical coupler. Fiber/multicore fiber 3020 ends with fiber interface unit 3022, e.g. optical coupler. Both interface units, 3032 and 3022 are held by interface bed unit 3060, which is part of disposable unit 304, as is explained in detail below. The ends of interface units 3022 and 3032 form the interface to reusable unit 302. The example described herein demonstrates optical coupling of the optical image transmitted by fiber 3020 and the light transmitted towards waveguide 3030, yet it would be apparent that other suitable means for coupling may be used and are within the ambit of the invention. On the other side of interface bed 3060 (the right side of it in the drawing), elements of reusable unit 302 are presented. Optical module 3050 is adapted to receive optical data transmitted by fiber 3020 and to convert it into digital representation of the image. Optical module 3050 ends, at its side facing interface bed 3060, with shaped protruding end that is adapted to assist in optically aligning fiber 3020 with the central optical axis of optical module, as is explained in detail below. Light source 3040 is disposed close to optical module 3050 and is substantially parallel to it, and its light beam is aimed towards light waveguide interface unit 3032. When reusable unit 302 is fully inserted and properly situated inside disposable unit 304, light source interface unit 3042, disposed at the front end of light source unit 3040, tightly interfaces with the rearmost end of waveguide interface unit 3032, thereby ensuring good transmission of the light to the wavegu ide.

Reference is made now to FIGS. 3A1 and 3A2, which are simplified schematic illustrations demonstrating aspects of the interface between disposable unit 304 and reusable unit 302, according to some embodiments of the invention. In order to ensure good enough optical coupling of the light transmitted to the endoscope insertion tube and of the optical image received from the optical guide, certain requirements need to be met. In the light path, good and efficient transfer of the light energy should be provided in order to minimize light energy loss in the interface between the light source interface unit 3042 and the waveguide interface unit 3032. As is known in the art, in order to minimize light loss during pass from medium to medium, both should have same refraction coefficient, or as close as possible to each other. This requirement can easily be satisfied by proper selection of the transparent materials used for production. In some embodiments, using light source disposed at the distal end of the endoscope, e.g., LED, instead of optical coupling for transmitting light to the endoscope, an electrical coupling may be used for providing electrical power to the LED.

In some embodiments of the invention, the layer at the interface plane may be as thin as possible so that light passing through it will experience minimal losses. In order to satisfy this requirement, light source unit is slidably disposed inside reusable unit 302 such that it may slide back and force parallel to an imaginary longitudinal axis (ILA) of reusable unit 302. Light source unit 3040 may be disposed with springy element 3048 supporting between light source 3040 and the body of reusable unit 302. When reusable unit 302 is not coupled with disposable unit 304, springy element 3048 is unloaded and the front end of light interface unit 3042 protrudes beyond light interface plane (LIP). When units 302 and 304 are coupled, light interface unit is pushed backwards by waveguide interface unit 3032, and springy element 3048 retracts and provides predetermined coupling force that ensures sufficient optical coupling for the light.

In order to ensure good transfer of images collected by fiber unit 3020 to optical module 3050, in addition to providing good light transmission at the interface plane, accurate transfer of the optical image should also be provided. When coupling optical image source and optical image destination units, the coupling should be set in three main axes X-Y-Z of the interface, so that the optical axes of the source and the destination are aligned and optical focus is provided. In order to ensure self-alignment of the optical axes when fiber interface unit 3022 and optical module 3050 are coupled, the interface plane of fiber interface unit 3022 may be shaped as a conical depression 3022A made with its wider opening facing the housing (such as housing 104A of FIG. 1A) of disposable unit 304. Fiber 3020 may end exactly in the middle of the narrower opening of conical depression 3022A. Waveguide interface unit 3022 may be slidably disposed in interface bed 3060 so that is free to slide in the X-Y plane of interface bed 3060, but maintains accurate location in the Z axis. Before coupling, interface unit 3022 may be located in the X-Y plane so that the center of conical depression 3022A is located approximately at the X-Y coordinates of the expected X-Y coordinates of the mutual optical axis of the coupled units 302 and 304. The front end 3052 of optical module 3050 may be formed as protrusion (e.g., a conical protrusion) that matches the conical depression 3022A in size of the wide and narrow bases and the cone angle. When reusable unit 302 is inserted into its housing in disposable unit 304 and approaches interface bed 3060, the front and narrower end of conical protrusion 3052 may enter into the wide opening of conical depression 3022A and gradually align its optical axis with that of fiber unit 3020, by enforcing the required movement(s) in the X-Y plane until fiber interface unit 3022 fully aligns with optical module 3050. Description of adjustment of the focus in this embodiment is described herein after.

Reference is made to FIG. 3A2, which is a schematic simplified block diagram of a focus unit for adjusting optical focus for the image transmitted by fiber unit 3020 to optical module 3050, when reusable unit 302 and disposable unit 304 are coupled. Mechanical accuracy of the reusable unit 302 may be ensured during production. However, the disposable unit 304 may be subjected to less accurate manufacturing standards, in order to reduce production costs. As a result, when reusable unit 302 and disposable unit 304 are coupled, the actual distance between the end of fiber interface unit 3022 and optical module 3050 may vary from one disposable unit to another one by unacceptable variations range. In order to ensure accurate focusing, optical module 3050 may be made with a transparent front face 3053 so that the light sensitive plane 3052' is located at an accurate pre-determined optical gap (PDOG) distance from front face 3053. Fiber interface unit 3022 may be disposed in interface bed 3060 with certain freedom of movement along Z axis and may be located so that, when units 302 and 304 are not coupled, its front end protrudes slightly forward (toward the housing of unit 302) of the image interface plane (IIP). Fiber interface unit 3022 may be made with certain flexibility of movement along Z axis and its movement backwardly (towards fiber unit 3020) may cause springy return force due to certain level of flexibility of the fiber unit. When reusable unit 302 is fully inserted into its place inside the housing in disposable unit 304, front face 3053 slightly pushes fiber interface unit 3022 backwardly against return force of fiber unit 3020. As a result, fiber interface unit is forced to touch front face 3053, and, thereby, the optical gap between fiber interface unit and optical module 3050 is guaranteed.

Reference is made now to FIG. 3B, which is a schematic illustration of the inside elements of the central part of endoscope 300, according to some embodiments of the invention. In order to ensure good optical coupling of light source 3040 with light waveguide interface 3032, light coupling self-adjustment means may comprise lighting unit 3044 coupled to sliding shaft 3046 which is pushed towards the front end of disposable unit 302 by springy element 3048. When reusable unit 302 is fully inserted into its housing in disposable unit 304, lighting unit 3044 is pushed back slightly by waveguide interface unit 3032 and causes springy element 3048 to retract and induce coupling force of lighting unit 3044 onto waveguide interface unit 3032.

In order to enable adjustment of optical focus in the interface between optical module 3050 and fiber interface unit 3022 (i.e., setting the distance between the units along the optical axis), a focusing unit may comprise springy element 3056 housed in a cavity 3054 made in optical module 3050. Springy element 3056 is disposed and designed to provide continuous force that pushes optical element toward the rear end of reusable unit 302. Optical module may be pushed forward toward the front end of reusable unit 302, as is explained herein below regarding FIG. 3C.

Reference is made now to FIG. 3C, which is a schematic illustration of the inside elements of the rear part of endoscope 300, according to some embodiments of the invention. Optical sensor 3072 (e.g., CMOS sensor) of optical module 3050 is made to be pushed forward by focus adjustment means 3070, which comprises threaded unit 3074 threaded in threaded housing 3076. Threaded housing 3076 is rotatably disposed within reusable unit 302 and ends on the outer rear face of reusable unit 302 with adjustment knob 3078. When adjustment of focus requires optical module 3050 be brought closer to fiber interface unit 3022, knob 3078 may be rotated by the user to force forward movement of optical module by turning knob 3078 in a direction that causes threaded unit 3074 to extract from threaded housing 3076. When the required direction of adjustment is the opposite, adjustment knob 3078 may be turned to the other direction, causing threaded unit 3074 to retract into threaded housing 3076 and allowing springy element 3056 to push optical element 3050 backwardly, so that the imaged object is focused on optical sensor 3072.

Figure 4A:
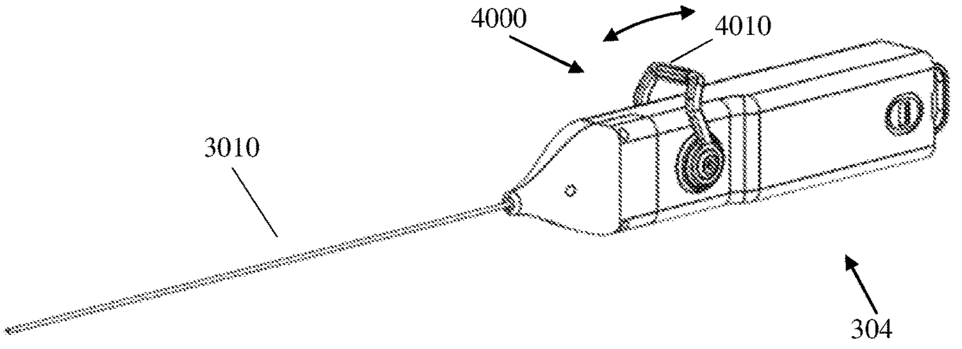
FIGS. 4A and 4B are a schematic isometric view of an endoscope showing a navigation lever of a shaft navigation system, and a view with removed cover of the front end of an endoscope depicting the shaft navigation mechanism, according to some embodiments of the invention.
Figure 4B:
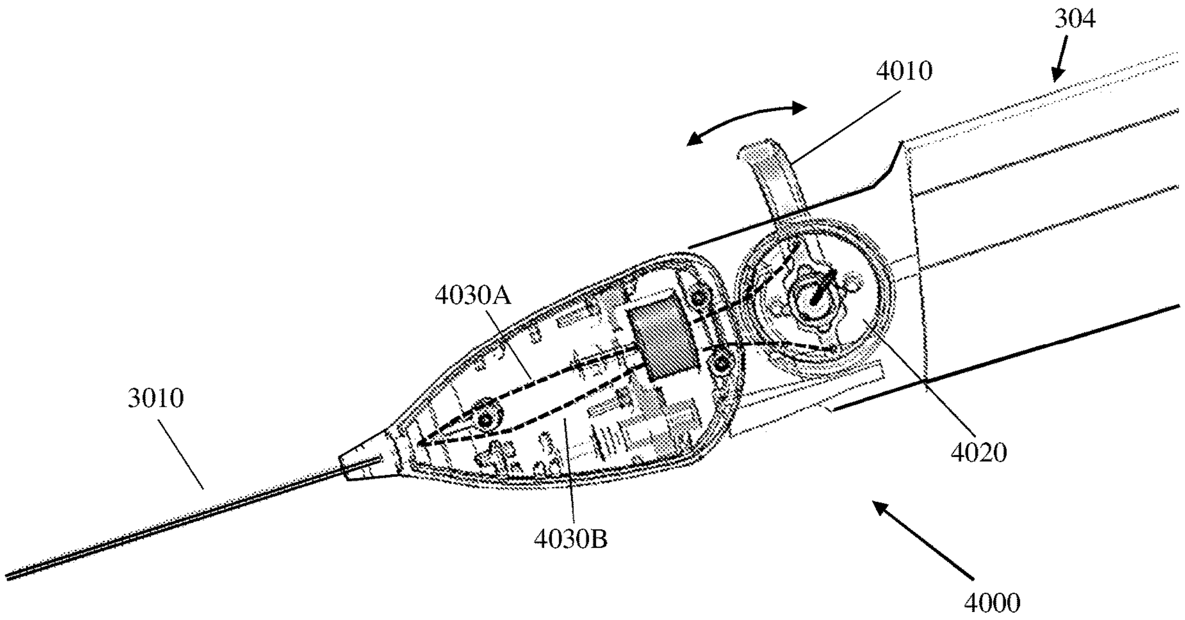

Reference is made now to FIGS. 4A and 4B, which are a schematic isometric view of endoscope 400 showing a navigation lever 4010 of navigation system 4000, and a view with removed cover of the front end of endoscope 400 depicting the navigation mechanism 4000, according to some embodiments of the invention. Navigation system 4000 is of the one-plane, two directions type, as is known for several types of endoscopes. This type of navigation is based on the difference in the pulling force applied onto one of the two navigation wires compared to that applied onto the other one. When the pulling force is equal, the endoscope will be in its "rest position". Navigation system 4000 comprises navigation lever 4010 that is disposed outside of the body of disposable unit 304 and is coupled by a common pivot to navigation disk 4020. Navigation wires 4030A and 4030B are connected, at a proximal end (shown in FIG. 4B) to navigation disk 4020, each on one side of the center of rotation of disk 4020, and at a distal end to either sides of the distal end of the insertion tube. When navigation level is moved by a user, it causes navigation disk 4020 to rotate and as a result to pull one of navigation wires 4030A/4030B and to release the other one. As a result, a difference in the forces exerted on the wires is applied, causing the distal end of the endoscopic insertion tube to bend in a first direction or in an opposite direction, and this way navigation can be performed. In order to direct the distal end of the endoscopic insertion tube in other directions, the user may rotate the reusable unit about the elongated axis, parallel to the direction of insertion of the endoscopic insertion tube.

Reference is made now to FIGS. 4C, 4C1 and 4C2, which are schematic partial isometric illustrations of a back cover of a disposable endoscope unit, in assembled and disassembled positions respectively, according to some embodiments of the invention. FIG. 4C depicts a disposable unit 4100 having main body 4110 and back cover 4120 shown in a back cover closed position, according to some embodiments of the invention. Back cover 4120 may be made to securely cover back opening 4122 (FIG. 4C1) for example after a reusable unit (not shown) is inserted into it. Back cover 4120 may be hingedly connected at one end to hinge rest 4116 on the outer circumference of opening 4112 by means of hinge 4126. Main part 4122 of back cover 4120 may comprise an opening 4128 in it, for example to allow endoscope cable to pass through it from the reusable unit outwardly. In order to securely lock back cover 4120 in its closed position, a locking mechanism may be used, comprising first locking member 4114 connected to disposable unit 4110 at one end and to second locking member 4124 at its other end. Second locking member 4124 may be equipped at its other end with locking pins 4124A adapted to tightly pull-and-close main cover unit 4122 when locking pins on locking dents 4125 and pull them towards main body 4110 of disposable unit 4100.

Figure 5:
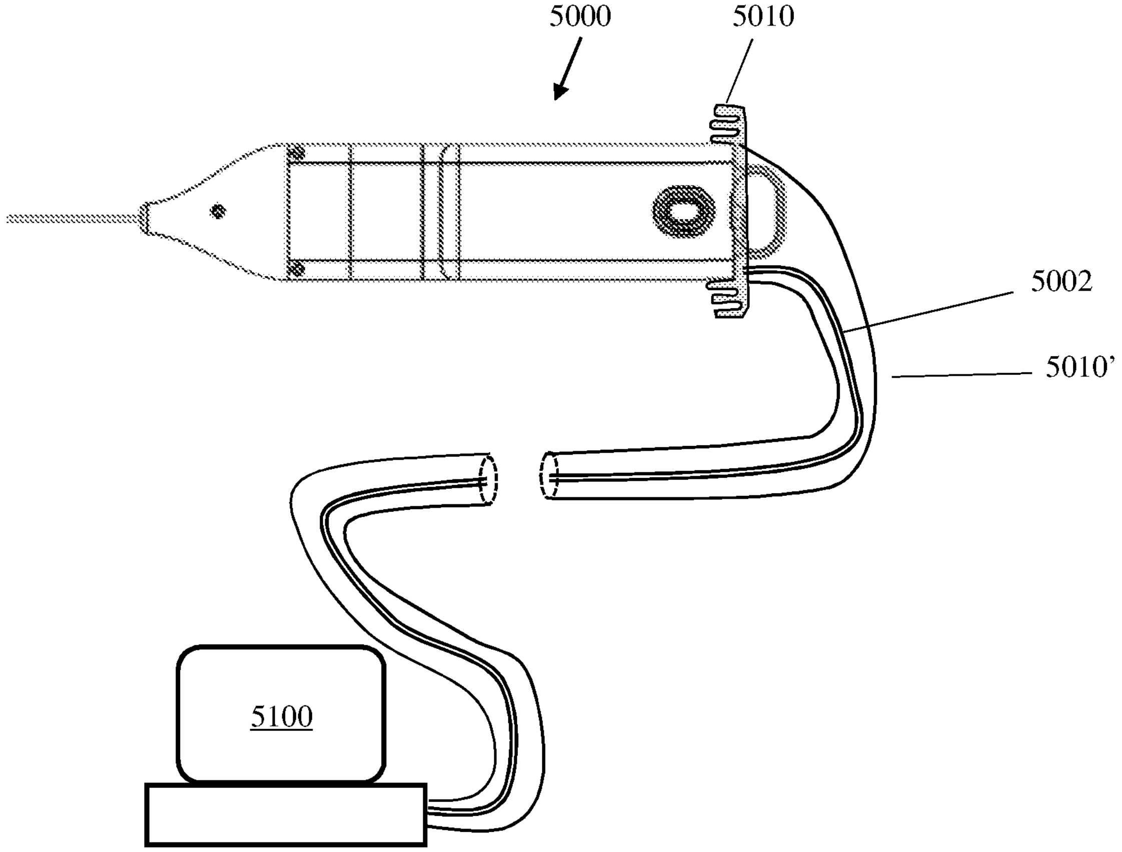
FIG. 5 a schematic illustration of a sleeve for preserving the required level of cleaning of the reusable part of an endoscope, according to some embodiments of the invention.

Reference is made now to FIG. 5, which is a schematic illustration of means for preserving the required level of cleaning of the reusable part of an endoscope, according to some embodiments of the invention. In order to enable reusing of a reusable unit, such as reusable unit 302, without having to undergo full and lengthy sterilization protocol after each use, it is essential to protect the reusable unit during an endoscopic procedure so that its required level of cleaning will not be tampered with. According to some embodiments of the invention, this requires to enable operation of the endoscope in a way that will ensure that reusable unit is protected along the entire procedure in a required level of cleaning, including during the separation of the reusable unit from the disposable unit after the procedure. According to some embodiments of the invention, disposable unit 5000 may be provided with a flexible thin sleeve 5010 that may be made of a sterilization-preserving material (e.g., as is used for sterilized gloves). Before use, sleeve 5010 may be disposed close to the opening of reusable unit housing (such as housing 104A of FIG. 1A) and may be in its folded position, for example it may be wrapped around the rear part of disposable unit like serpentine. Sleeve 5010 may have a length, in deployed position, substantially equal to the length of the endoscope cable that connects the endoscope to its control unit 5100 (e.g., about 3 meters). After insertion of a reusable unit into disposable unit 5000 sleeve 5010 may be unfolded and stretched along cable 5002 (described as 5010') until the cable is fully or substantially fully covered. After the endoscopic procedure, the user may hold the end of sleeve 5010' and carefully pull it back toward disposable unit 5000 without tampering with the sterilization of cable 5002. After sleeve 5010' has been folded back fully and optionally rolled over the rear end of reusable unit 5000 with its inside facing out, the rear end the reusable unit (not shown in this drawing) is revealed. At this stage, the user may use a sterilized hand, of himself or of another colleague, to carefully pull the reusable unit out of its housing in disposable unit 5000, using for example pull-out means, such as pull-out means 102C of FIG. 1A. After the reusable unit has been removed and disposable unit 5000 has been taken away, the risk of tampering with the sterilization of the reusable unit by the disposable unit ends, and the process may end until reuse of the reusable unit.

Figure 6:
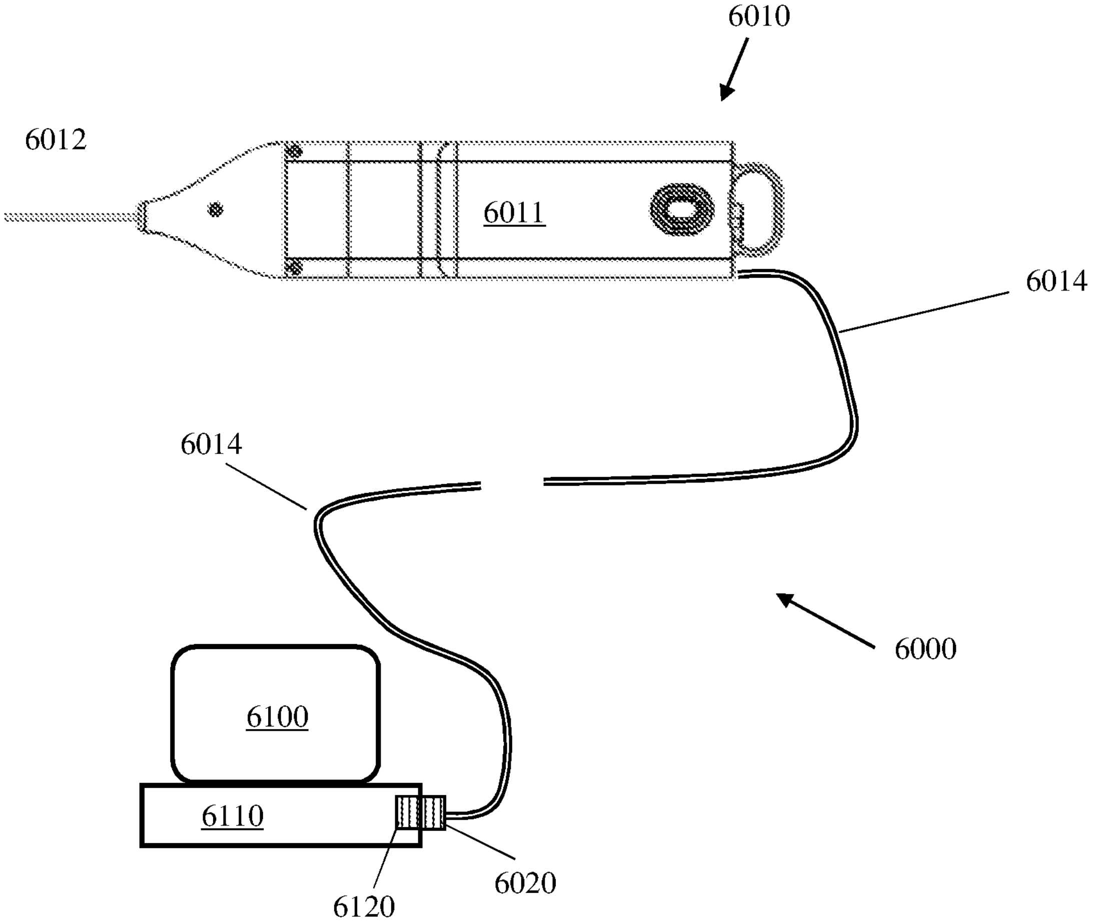
FIG. 6 schematically depicts means for preserving the required level of cleaning of reusable endoscopic equipment while using disposable endoscope insertion tube according to some embodiments of the invention.

Reference is made now to FIG. 6, which schematically depicts endoscope system 6000 comprising a reusable endoscopic equipment unit 6110 and a disposable endoscope 6010, according to some embodiments of the invention. Disposable endoscope 6010 may comprise endoscope insertion tube 6012, that may comprise fiber unit (single or multi-core fiber), optional optical means (e.g., lens), lighting means (either disposed at the distal end or at the proximal end of the endoscope, endoscope handle 6011, endoscope cable 6014 and disposable endoscope connector 6020. Cable 6014 may comprise optical guiding means to provide the optical image acquired at the distal end of disposable endoscope to connector 6020 (e.g., the fiber unit may extend from the distal end to connector 6020). Cable 6014 may further comprise electrical conduit to power the lighting means of disposable endoscope 6010, or light guide to enable transmission of light from a light source disposed in reusable endoscopic equipment 6110 to reach the distal end of endoscope insertion tube 6012. According to this embodiment, disposable endoscope 6010, extending from the distal end of insertion tube 6012 to connector 6020, may be disposed of after use in a medical procedure for a first patient, and another, pre-sterilized disposable endoscope 6010 may be connected to reusable endoscopic equipment unit 6110 via connector 6120 and connector 6020. The specific details of the connections inside connectors 6120 and 6020 may vary according to the specific embodiment. For example, connectors 6120 and 6020 may comprise optical interface to support providing of the optical image acquired at the distal end of insertion tube 6012 to the optical receiver in reusable endoscopic equipment unit 6110. Connectors 6120 and 6020 may comprise optical interface to enable providing of light produced by lighting means disposed in reusable endoscopic equipment unit 6110 to be conveyed to the distal end of disposable endoscope 6010, or in another embodiment the connectors may comprise electrical interface to enable powering a light source disposed in disposable endoscope 6010.

In some embodiments disposable endoscope 6010 may comprise navigation means (not shown), for example like navigation means system 4000 that was described in conjunction with FIGS. 4A and 4B.

According to this embodiment, sterilization of reusable endoscopic equipment unit 6110 may not need any special sterilization preserving means. Typically, control unit 6100 and reusable endoscopic equipment unit 6110 are located distal from a treated patient, and the end of cable 6014 that is connected to connector 6020 is not likely to be contaminated during the endoscopic procedure. Nevertheless, at the end of an endoscopic procedure, disposable endoscope 6010 may be disconnected from reusable endoscopic equipment unit 6110 without tampering with its sterilization, thereby enabling further uses of reusable endoscopic equipment unit 6110 without needing to sterilize it after each endoscopic procedure.

According to some embodiments of the invention, reusable endoscope unit may be used with a variety types of disposable endoscope insertion tubes, for a large variety of needs and goals. The various types of disposable insertion tubes should only comply with the interface design of the reusable unit mechanically and optically.

In some embodiments, the disposable unit of the endoscope may comprise, disposed at the distal end of the endoscope insertion tube or at its proximal end, a videoscope unit for acquiring the object image and to transmit it to the endoscope reusable unit by means of data signals.

The conversion of the optical image at the proximal end of the multicore fiber to digital image data may be done, according to some embodiments, by providing an optical sensor at the proximal end of the optical guide of the endoscopic insertion tube and converting the optical image to digital data, e.g., by means of rolling shutter technique as is known in the art. A communication interface may be provided to facilitate coupling of the optical sensor to a receiver in the reusable unit and transmitting the digital data from the optical sensor to the receiver.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An endoscope device comprising:

a disposable unit comprising:

an endoscopic insertion tube comprising an optical guide configured to transmit an image data of a distal object, having a proximal end and a distal end, and comprising light waveguide for illuminating the distal object;

an interface unit; and a housing defining a confined space and a rear opening; and a reusable unit configured to be disposed and secured inside the confined space of the housing of the disposable unit, the reusable unit comprising a receiver to receive, via the interface unit, the image data of the imaged distal object, wherein the reusable unit is configured to be slidably fitted, via the rear opening, into the confined space of the housing, to be sealingly accommodated and within the housing of the disposable unit, with a front outside surface, adjacent to the endoscopic insertion tube and lateral surfaces of the reusable unit encased by the housing, and a light source slidably disposed within the reusable unit, such that the light source is slidable back and forth parallel to an imaginary longitudinal axis, with a springy element supporting between the light source and a body of the reusable unit, such that, when the disposable unit and the reusable unit are coupled, the light source is pushed backwards and the springy element provides a coupling force between the light source and an interface of the light waveguide interface so as to ensure optical coupling to the light waveguide of the disposable unit;

wherein the interface unit comprises an interface bed for holding a first interface between the light source and the light waveguide and for holding a second interface between the receiver and the optical guide.

2. The device of claim 1, wherein the interface unit comprises an optical coupler.

3. The device of claim 2, wherein the receiver is adapted to receive an optical image from the optical guide via the optical coupler and to convert it to digital image data.

4. The device of claim 3, wherein the receiver comprises an optical sensor.

5. The device of claim 1, wherein the disposable unit further comprises a navigation mechanism comprising a navigation lever connected to a disk that is connected to navigation wires for manipulating a distal tip of the insertion tube.

6. The device of claim 1, wherein the optical guide comprises a multicore fiber.

7. The device of claim 1, further comprising a focusing unit for enabling focusing the image by means of controlling the distance between the proximal end of the optical guide and the receiver, the focusing unit comprising:

a springy element for applying a continuous force to push an optical element towards a rear end of the reusable unit, and an adjustment knob for moving a threaded housing in which the optical element is placed.

8. The device of claim 1, further comprising an aligning device for aligning of the proximal end of the optical guide with an optical axis of the receiver.

9. The device of claim 1, further comprising an extendable sterilization protecting flexible sleeve configured to be rolled off an aft end of the disposable unit and enclose a cable leading from the reusable unit to a control unit.

10. The device of claim 1, wherein, when the reusable unit is situated inside the housing, the opening of the housing is sealingly covered by a rear cover of the reusable unit.

11. The device of claim 1, wherein, when the reusable unit is situated inside the housing, the opening of the housing is sealingly covered by a rear cover of the disposable unit.

* * * * *